May 26, 1964 F. J. GRISANTI Plant Pat. 2,405
GRAPE PLANT
Filed Sept. 21, 1960
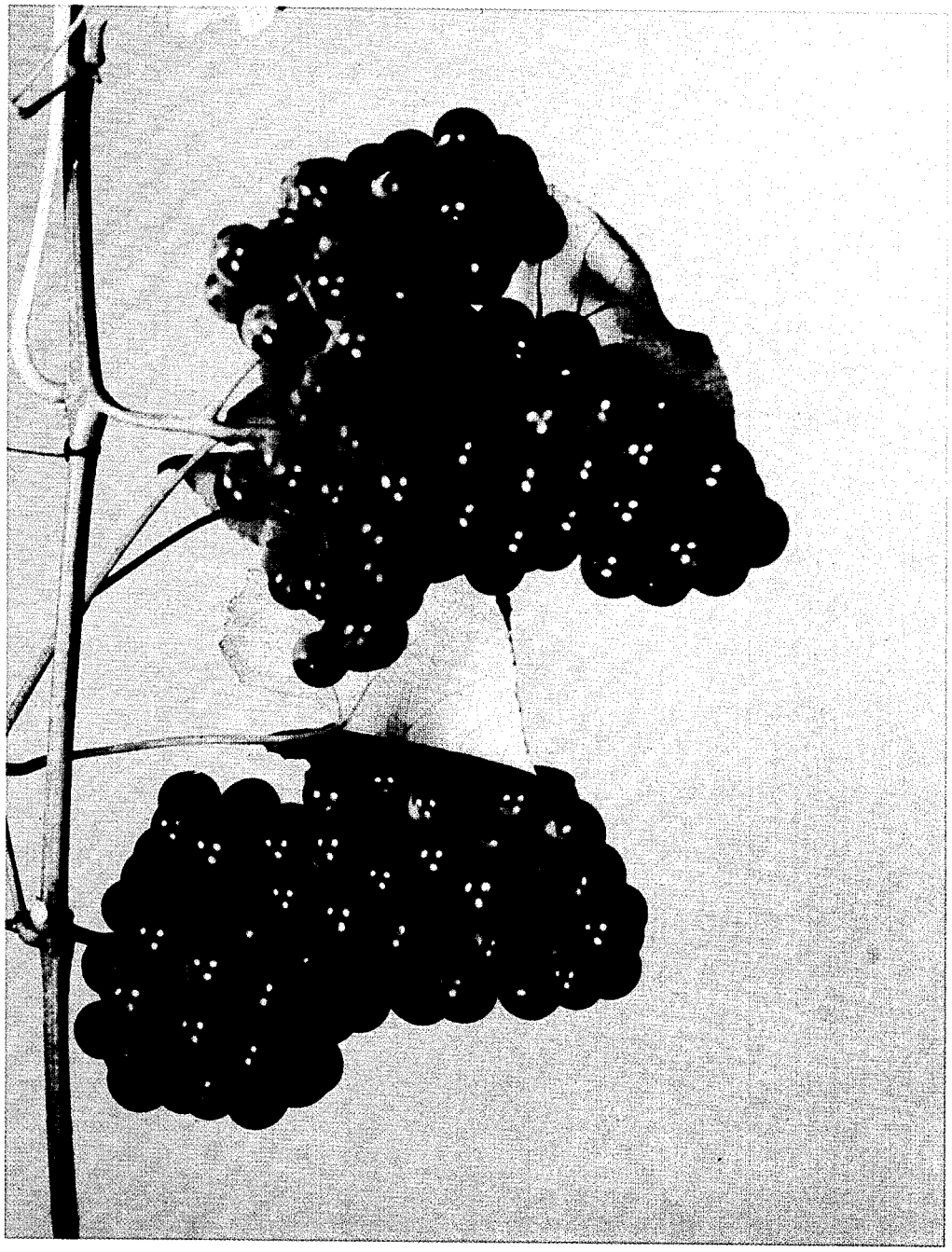
INVENTOR
Frank J. Grisanti,
BY
Bean, Brooks, Buckley & Bean.
ATTORNEYS.

United States Patent Office

Plant Pat. 2,405
Patented May 26, 1964

2,405
GRAPE PLANT

Frank J. Grisanti, Prospect Road, Forestville, N.Y.

Filed Sept. 21, 1960, Ser. No. 57,598
1 Claim. (Cl. Plt.—47)

The present invention relates to a new and distinct variety of grape plant.

The fruit of this variety is similar to Fredonia or Concord grapes but grows in clusters which are very much larger than Fredonia or Concord grapes. The fruit has excellent keeping qualities. The flavor and eating qualities are excellent, the grapes being somewhat sweeter than Fredonia grapes.

The enclosed drawing and the following specification present the distinctions in physical and botanical characteristics of the new variety of plant of my invention, which plant has been asexually reproduced by me on my farm at Forestville, in the township of Hanover, county of Chautauqua, State of New York.

The accompanying drawing shows a portion of a specimen plant as grown by me in the township of Hanover, county of Chautauqua, State of New York, the same bearing two typical fruit clusters.

The grape plant of my invention grew as a chance somatic mutation (a sport) of Fredonia grape stock. I have produced other plants from this chance somatic mutation by layering or tipping, likewise on my farm at Forestville, in the township of Hanover, county of Chautauqua, State of New York. The original mutation and the subsequent plantings both occurred on land owned by me from a time long prior to the occurrences described above and which I still own, such land being located on Prospect Road, in the township of Hanover, county of Chautauqua, State of New York.

The plant of my invention has been asexually reproduced by me in the State of New York, in the township of Hanover, in the manner common to asexually reproducing varieties of grape plants, that is by layering or tipping.

At maturity the plants are of substantially the same appearance and characteristics as those of Fredonia or Concord grapes but are distinguished very substantially by the extremely large fruit clusters which they bear. The plants grown as described herein exhibit the qualities and characteristics set forth in this specification as grown in the sunny and cool climate in western New York, conditions being moderately moist.

The chance somatic mutation mentioned above was found in a cultivated vineyard on my aforesaid farm.

The following is a detailed description of my new variety of grape plant grown as described above. In the following description the color designations are from Maerz and Paul's "Dictionary of Color" and the figures in parentheses are averages of all specimens measured.

Plant: Large and vigorous, growing like the Fredonia grapevine and differing from it principally in the extremly large fruit clusters which it bears.

Propagation: By layering or tipping at Forestville, New York on Grisanti land.

Environment: Rolling hillsides; sunny, warm temperate climate with cold, moist winters and warm summers.

Shoots: Essentially as in Fredonia; but the internodes change in color from green to the characteristic reddish-brown color in fall about one week earlier than the comparable change in the Fredonia grapevine. Budding-out of canes and elongation of the shoot in the spring occur about ten days later than in Fredonia and Concord.

Leaves: Essentially as in Fredonia and Concord: large, glabrous on the upper side with occasional short hairs on the veins; the lower side, including veins and interveinal areas, tomentose except on the very largest veins, which are essentially glabrous.

Flowers: In a compound panicle or thyrse as in Fredonia, Little Fredonia and Palmer Fredonia, but the panicle is larger and there are more flowers per panicle. Flowering occurs from 7 to 10 days later than in Concord or Fredonia. The panicle at general anthesis measures 69–(103)–120 mm. in length (not including the basal stalk or peduncle), whereas Fredonia in this measurement is 38–(59)–69 mm. Basal stalk or peduncle of the flower cluster averages 44 mm. in length at anthesis, whereas the basal stalk of Fredonia under similar conditions averages 22 mm. in length. The first or most proximal branch of the flower cluster, as in Fredonia, is more elongate than the others, is frequently in part abortive and tendril-like.

(*a*) Pedicels green, glabrous, 1.8–3.2 mm. in length.
(*b*) Calyx very minute, reddish brown and dry at anthesis.
(*c*) Corolla forming a green to brownish cap about 2.0–2.4 mm. in length which falls at anthesis, exposing the internal fertile organs.
(*d*) Stamens somewhat bent within the confining corolla, the filaments measuring about 1.8–2.5 mm. in length, the anthers attached by their outer face to the filaments.
(*e*) Pistil green and flask-shaped, measuring 1.6–2.2 mm. in length at pollination. Glands at base of pistil conspicuous, yellowish.

Fruit:

(*a*) Fruiting peduncle measures in cross-section diameter 4.5–(5.0)–5.5 x 5.2–(5.6)–6.2 mm. whereas comparable measurements of Fredonia are 2.1–(3.6)–3.8 x 4.0–(4.6)–5.0 mm.
(*b*) The fruit cluster at harvest is much larger than that of Fredonia, Palmer Fredonia, Little Fredonia or Concord, commonly exceeding two pounds in weight. My grapevine is, therefore, a large-clustered form whereas Palmer Fredonia and Little Fredonia are large-berried but relatively small clustered forms. Average of 11 measured bunches yielded an average length (measured from the proximal end of the proximal grape to the distil end of the terminal grape) of 159.6 mm., and average transverse circumference or "girth" (at the point of maximum circumference) of 304.0 mm. These were not randomly selected but did include both large and small bunches. Extreme measurements of these eleven measured bunches were as follows: 90–202 mm. in length, 180–432 mm. in circumference. Comparable measurements of twenty randomly sampled Fredonia bunches yielded averages of 110.3 mm. in length, 192 mm. circumference at the point of maximum circumference. Table 1 gives a summary of these and other measurements, including the weight of bunches at harvest and the weight of 100 randomly picked fruits each of my grape plant and of Fredonia grape plant.
(*c*) Color of mature fruit is Geneva Blue (C12), but glaucous areas on the fruit (where sheen is not rubbed off) correspond best in color with A9, near Blue-Aster.
(*d*) Keeping quality: excellent.
(*e*) Shipping quality: excellent.
(*f*) Picking quality: excellent.
(*g*) Flavor: excellent (sweeter than Fredonia).
(*h*) Eating quality: excellent.
(*i*) Length of the picking season: similar to Fredonia.
(*j*) Productivity per vine: upwards of 30 pounds.

*Table 1.—Dimensions at Harvest of My New Grape Plant as Compared With Fredonia Grapes*

| | My Grapes | Fredonia Grapes |
|---|---|---|
| Cross-section diameter of fruiting peduncle measured at widest point (just proximal to the first or tendril-like branch). | 4.5-(5.0)-5.5 x 5.2-(5.6)-6.2 mm. | 2-1-(3.6)-3.8 x 4.0-(4.6)-5.0 mm. |
| Average length of fruit bunch | 159.6 mm | 110.3 mm. |
| Average girth or circumference at maximum girth, of fruit bunch. | 304 mm | 192 mm. |
| Extreme weights of bunches measured | 65-848 g | 17-275 g. |
| Average weight of bunch | 539 g | 121 g. |
| Average weight of 100 randonly picked fruits. | 4.08 g | 3.85 g. |
| Number of seeds per fruit | 1-4 | 1-4. |

Under field conditions at Forestville, in the township of Hanover, county of Chautauqua, State of New York, the productivity of the variety of grape plant of the present invention is much greater than than of any similar variety known to me.

I claim:

A new and distinct variety of grape plant, substantially as herein shown and described, characterized particularly as to novelty by the extremely large clusters of fruit which said plant bears.

No references cited.